United States Patent
Schilowitz et al.

(10) Patent No.: US 6,876,193 B2
(45) Date of Patent: Apr. 5, 2005

(54) METHOD FOR DECONVOLUTION OF IMPEDANCE SPECTRA

(75) Inventors: Alan M. Schilowitz, Highland Park, NJ (US); Walter D. Vann, Marlton, NJ (US); Limin Song, West Windsor, NJ (US); John S. Szobota, Morristown, NJ (US); Alexander Bolkhovsky, Aston, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/885,272

(22) Filed: Jul. 6, 2004

(65) Prior Publication Data

US 2005/0035755 A1 Feb. 17, 2005

Related U.S. Application Data

(60) Provisional application No. 60/494,485, filed on Aug. 12, 2003.

(51) Int. Cl.$^7$ .............................................. G01R 31/08
(52) U.S. Cl. ..................................... 324/158.1; 324/520
(58) Field of Search ............................. 324/158.1, 520, 324/633, 667, 674, 681, 707, 698

(56) References Cited

U.S. PATENT DOCUMENTS 5,595,680 A * 1/1997 Bryant et al. .................. 252/77
6,645,403 B1 * 11/2003 Park et al. .................. 252/270

* cited by examiner

*Primary Examiner*—David Zarneke
*Assistant Examiner*—Trung Q. Nguyen
(74) *Attorney, Agent, or Firm*—Ramesh Varadaraj

(57) ABSTRACT

A method for deconvoluting a time dependent impedance spectrum and using the deconvoluted time dependent impedance spectrum as an indicator of the performance condition of a working fluid is disclosed. Also disclosed is a method to determine the viscosity ratio of a working fluid using the resistance ratio obtained from frequency dependent impedance data.

8 Claims, 4 Drawing Sheets

METHOD FOR DECONVOLUTION OF IMPEDANCE SPECTRA

This application claims the benefit of U.S. Provisional application 60/494,485 filed Aug. 12, 2003.

BACKGROUND OF THE INVENTION

The present invention is broadly concerned with deconvolution of impedance spectra of a working fluid. The invention is also concerned with using deconvoluted impedance spectra as an indicator of the performance condition of a working fluid.

SUMMARY OF THE INVENTION

Working fluids, such as lubricating oils and hydraulic fluids, are important components of a wide variety of mechanical systems in which they provide one or more functions such as lubricating moving parts, transferring force or energy on the mechanical system, protecting parts against wear or even a combination of these. These fluids typically consist of hydrocarbon base oil formulated with numerous performance additives selected to enhance one or more performance characteristics of the fluid. With use over time these fluids may become contaminated with substances with which they come into contact, by the ingress of foreign substances in the mechanical system, by oxidation of the base oil and chemical decomposition of the additives used in the formulated fluids. The net result is a decrease in the performance characteristics of the fluid with the concomitant negative impact on the mechanical system using the fluid.

Therefore, in many industrial environments regular fluid analysis by common laboratory methods is a standard modus operandi. This necessitates obtaining a sample of the fluid and transporting it, typically off-site, for analysis. This procedure normally takes at least three full days before the requisite analysis is completed and a report can be obtained. Such a time lag is highly undesirable. Many proposed methods for the on-line evaluation of the quality of lubricants are based on electrical measurements, such as the dielectric constant or impedance of the fluid, with the measurements being taken at one fixed frequency or a multiplicity of frequencies. Since the best frequency for optimum sensitivity often depends on the properties or operational conditions of the working fluid it is preferred to make impedance measurements at a multiplicity of frequencies. One subset of impedance measurements is dielectric measurements.

Data obtained from time dependent impedance measurements are generally extremely complicated or convoluted. Additive degradation, base oil oxidation, temperature change, water and other polar species contamination, and viscosity changes of the lubricant oil can impact impedance properties of a lubricant oil. A method to deconvolute time dependent impedance spectra is needed so that the deconvoluted time dependent impedance spectra can provide information about the lubricant.

One object of the present invention is to provide a method for deconvolution of time dependent impedance spectra.

Another object of the present invention is to provide a method to utilize deconvoluted time dependent impedance spectra as an indicator of the performance condition of a fluid.

Yet another object of the invention is a method to determine the viscosity ratio of a fluid by measuring frequency dependent impedance spectra.

These and other objects will become apparent from the description, which follows.

In one embodiment of the invention is a method to deconvolute a complex time dependent impedance spectrum of a lubricant oil comprising:

obtaining a time dependent impedance spectrum of the lubricant oil over a time range and at a plurality of time intervals wherein the time dependent impedance spectrum comprises at least one peak, measuring at least one lubricant property over said time range and said plurality of time intervals to provide at least one time dependent lubricant property spectrum wherein the time dependent lubricant property spectrum comprises at least one peak, comparing said obtained time dependent impedance spectrum with said measured time dependent lubricant property spectra, where the peaks of each coincide in time, assigning to the peaks on the time dependent impedance spectrum the lubricant property of said measured coinciding time dependent lubricant properties, resulting in a deconvoluted time dependent impedance spectrum.

In another embodiment of the invention is a method to use a time dependent spectrum as an indicator of the performance condition of a lubricant oil comprising:

obtaining a time dependent spectrum of the lubricant oil over a time range and at a plurality of time intervals, wherein said spectrum comprises at least one peak and said spectrum is selected from the group consisting of impedance spectrum, admittance spectrum, resistance spectrum, capacitance spectrum, phase angle spectrum and dielectric spectrum, measuring at least one lubricant property over said time range and at said plurality of time intervals to provide at least one time dependent lubricant property spectrum having at least one peak, comparing said obtained time dependent spectrum with said measured time dependent lubricant property spectrum, where the peaks of each coincide in time, assigning to the peaks on the time dependent spectrum the lubricant property of said measured coinciding time dependent lubricant properties whereby the time dependent spectrum is used an indicator of the measured lubricant property, and where the peaks of each do not coincide in time the time dependent spectrum is used as an indicator of reduced performance condition of the lubricant oil.

In yet another embodiment of the invention is a method to determine the viscosity ratio (VR) of a lubricating oil in a machinery comprising:

measuring frequency dependent impedance data for the lubricating oil over a range of frequencies and over a time range, determining the resistance (R) of the lubricating fluid using a Nyquist plot, at starting time t=0 and a particular time, t within said time range, and denoting the resistance at time t=0 as $R_o$ and the resistance at time t as $R_t$, calculating a resistance ratio $RR=R_t/R_o$, measuring the absorbance (A) of the lubricating oil at said time, t at a wavelength in the range of 500 to 1050 nm, calculating the value of $\{RR+C1+C2(A-C3)\}/C4$ where C1, C2 and C3 are numbers whose absolute values range from 0 to 10,000, and C4 is a number whose absolute values range from 0.005 to 10,000, said determined value being the viscosity ratio (VR) of the lubricating oil.

DETAILED DESCRIPTION OF THE PREFERRED EMBODIMENTS

AC (alternating current) electro-impedance spectroscopy is a well-known technique. It involves the imposition of AC signals over a broad range of frequencies to a material to be analyzed. The electrical response to those signals is determined and by the application of electric circuit theory a description of the properties of the material is obtained.

AC electro-impedance spectroscopy can be used to determine the conditions of a working fluid, particularly the conditions of low conductivity oils. Examples of low conductivity oils are oils that have a kinematic viscosity at 100° C. of greater than 15 cSt and containing less than about 3 wt % (active basis) of additives selected from dispersants, antioxidants, detergents, VI improvers and antiwear agents. AC electro-impedance spectroscopic methods can also be used for determining the condition of industrial oils, especially on-line, i.e., when contained in mechanical systems, even when the systems are operating. Non-limiting examples of working fluids are fluids such as paper machine lubricating oil and turbine oil.

Typically AC electro-impedance spectra of a fluid can be measured when a pair of spaced apart electrodes, such as concentric, cylindrical electrodes, are placed in a body of working fluid to be analyzed. Preferably the working fluid is within a mechanical system, for example in an oil reservoir or sump of a mechanical system, in an oil delivery manifold, or bypass manifold of a mechanical system requiring lubrication or use of a working fluid.

Figure 1:
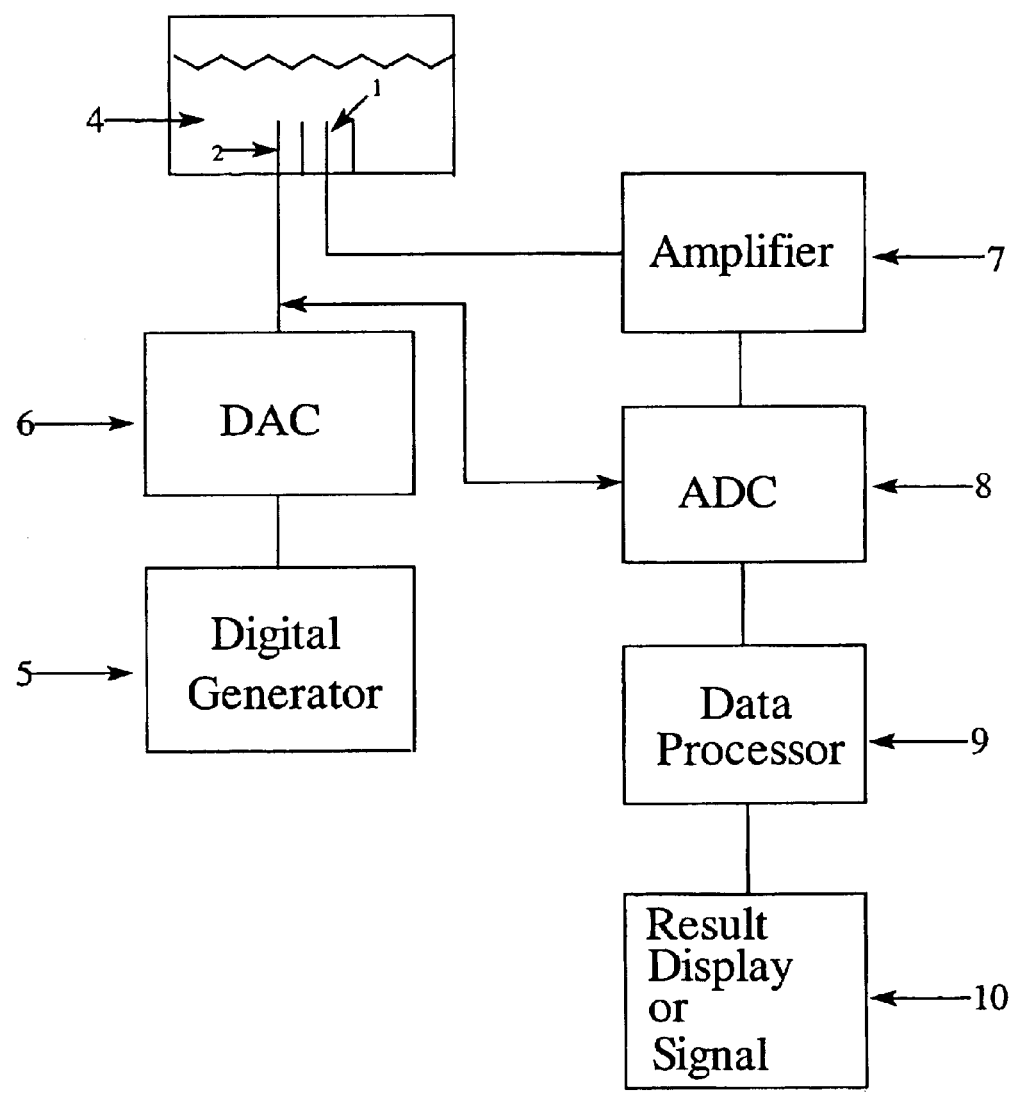
FIG. 1 is a schematic illustration of a system for monitoring the condition of a working fluid according to the invention.

The dimensions of the electrode, of course, will depend on its positioning within the mechanical system and the nature of the working fluid being analyzed. For industrial lubricants, such as paper machine oils, the length of the electrodes shown in FIG. 1 typically will be in the range of between about 0.5 cm to about 20 cm, the diameter of the outer electrode between about 0.5 cm to about 4 cm and the gap between the inner and outer electrode between about 0.1 to 10 mm. Other geometries for the electrodes may be employed, such as flat parallel plates, flat interdigitated electrodes etched on an inert substrate and the like.

Placing the electrodes in a working fluid contained in a mechanical system permits on-line, real time, analysis of the fluid, i.e., the condition of the fluid can be measured continuously while employed in the mechanical system without the need to remove a sample of the fluid from the system for analysis.

An AC signal is applied to one electrode at a plurality of frequencies, typically at more than two frequencies, preferably at more than three frequencies, for example from 3 to 1000 frequencies and preferably from 4 to 20 in the range of from 1 Hz to 1 M Hz. The applied signal produces an electrical output at the other electrode, which is measured. A device for applying the signal and measuring the output is a frequency response analyzer (FRA). Such frequency response analyzers are commercially available devices and are used to acquire frequency dependent impedance data. Another fluid impedance monitor is shown schematically in FIG. 1 where 1 and 2 represent concentric electrodes immersed in an oil 4. A digital function generator 5 generates a predetermined discrete sequence of signals and a digital-to-analog converter 6 converts the sequence to an analog sinusoidal voltage of small amplitude, Vn, and frequency, $\omega$, and applies the voltage to the outer electrode 2. The applied signal produces an electrical charge on the inner electrode 1. A charge amplifier 7 converts the charge into a sinusoidal voltage, Vout, at the same frequency, $\omega$. The time-based waveforms of both input and output voltages are converted by an analog-to-digital converter 8 and the resulting data is acquired and processed by data processor 9.

In the data processor 9, a digital frequency response analyzer is used to obtain the complex transfer function of the output voltage with respect to the input voltage, i.e., the ratio of the complex amplitude of the sinusoidal output voltage to that of the sinusoidal input voltage. This complex transfer function is equal to the ratio of the feedback impedance of the charge amplifier 7 to the impedance of the working fluid to be analyzed. Dividing the transfer function by the known amplifier feedback impedance, the admittance of the working fluid is obtained. The reciprocal of the admittance is equal to the impedance of the working fluid. The process of data acquisition and processing can be repeated over all operating frequencies over a period of time.

Time Dependent Impedance Spectra

In a simple acquisition and processing mode, the process of data acquisition and processing can be made over a period of time at a fixed frequency. Impedance plotted as a function of time at a fixed frequency provides a time dependent impedance spectrum. Impedance plotted as a function of time over a multiplicity of frequencies provides a series of time dependent impedance spectra. One can also plot admittance instead of impedance and obtain a series of time dependent admittance spectra. Time dependent impedance spectra are preferred.

Frequency Dependent Impedance Spectra

Figure 2:
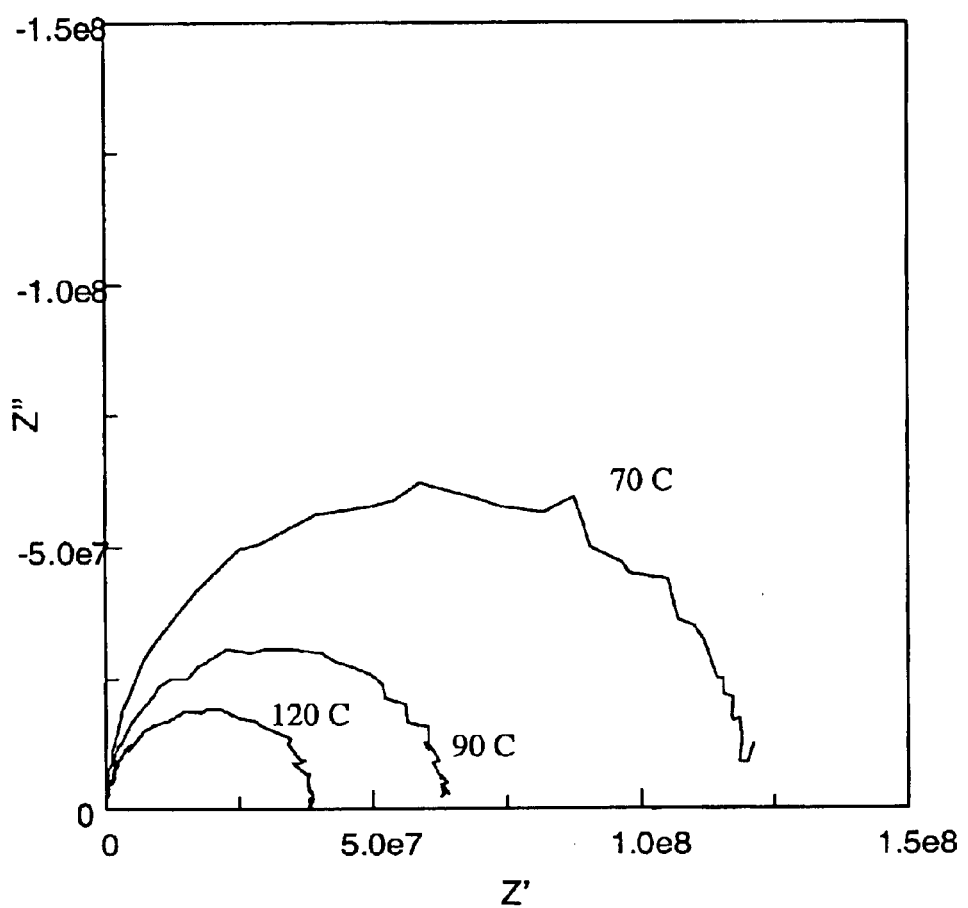
FIG. 2 is a series of Nyquist plots for a paper machine lubricant. The Y axis is the negative of the imaginary part of impedance, Z" and the x axis is the real part of impedance, Z'.

In a preferred embodiment the AC signal is applied at a plurality of frequencies, for example from 3 to 1000 frequencies and preferably from 4 to 20 in the range of from 1 Hz to 1 M Hz and frequency dependent impedance or admittance data are obtained. These frequency dependent impedance or admittance data are used to determine one or more of the resistance, the capacitance, the frequency at which the phase angle between the voltage and current is 45° (Omega max), the time constant of the working fluid and dielectric constant. This can be achieved, for example, by plotting the frequency dependent impedance data in the form of a Nyquist plot where, in rectangular coordinates, imaginary impedance $(Z''=im(Z)=[Z]Sin(\Theta))$ is plotted against real impedance $(Z'=re(Z)=[Z]Cos(\Theta))$ or, in polar coordinates, $|Z|=[(Z')^2+(Z'')^2]^{1/2}$ is plotted against $\Theta$, the phase difference between voltage and current. Examples of Nyquist plots are shown in FIG. 2 for a paper machine lubricant. In FIG. 2, the Y axis is the negative of the imaginary part of impedance, Z" and the x axis is the real part of impedance, Z'.

Preferably the Nyquist plot of frequency dependent impedance data is further analyzed by fitting the data to a least-squares best fit curve. Such a curve can be fit using many standard data analysis packages. The resistance of the oil/electrode system can then be calculated by determining the diameter of the curve along the x axis. The frequency at which $\Theta$ reaches 45 degrees is known as Omega max. The reciprocal of Omega max is the time constant, RC. The capacitance may then be determined using relations, Omega max=1/RC. Alternately, by choosing a frequency that is sufficiently high, for example by choosing a frequency greater than about 10,000 Hz, the capacitance can be approximated from a single impedance measurement. Dielectric constant is defined as the ratio of capacitance of the electrode in the fluid to the capacitance of the electrode in a vacuum. By measuring the capacitance and knowing the capacitance of the electrode in a vacuum the dielectric constant of the fluid is calculated.

The frequency dependent impedance data can be measured for three, preferably for four or more values of $\Theta$ spanning a range of at least 45 degrees and a partial Nyquist curve is constructed from that data. This portion of the curve can then be analyzed with a standard least squares fitting program by assuming that the Nyquist plot follows an elliptical curve. The entire Nyquist curve can then be constructed by extrapolating to $\Theta$ values of zero and 180 degrees. At the same time values for capacitance, resistance and Omega max can also be determined.

Deconvolution of Time Dependent Impedance Spectra

The time dependent impedance or admittance spectrum of a working fluid is generally complicated or convoluted. Such a complicated or convoluted spectrum is of limited utility. In one embodiment of the invention is a method to deconvolute a time dependent impedance spectrum of a lubricant oil. A time dependent impedance spectrum of the lubricant oil is obtained over a time range and at a plurality of time intervals wherein the time dependent impedance spectrum comprises at least one peak. Preferably simultaneously, is measured at least one lubricant property, preferably at least two lubricant properties, for the lubricant oil over the same time range and plurality of time intervals to provide at least one or preferably a plurality of time dependent lubricant property spectra. The next step involves comparing the obtained time dependent impedance spectrum with the measured at least one or a plurality of time dependent lubricant property spectra. Where the peaks of each coincide in time, to the peaks on the time dependent impedance spectrum is assigned the lubricant property of the measured coinciding time dependent lubricant properties, resulting in a deconvoluted time dependent impedance spectrum.

A series of lubricant properties include but are not limited to properties such as additive degradation, base oil oxidation, temperature change, water and other polar species contamination, and viscosity changes of the lubricant oil. It is preferred to determine the time dependent impedance spectrum and the time dependent lubricant properties on-line. By on-line is meant during operation of the machinery comprising the working fluid. The time dependent impedance spectrum can be determined at one frequency or a multitude of frequencies. It is preferred to determine the time dependent impedance spectrum at a multitude of frequencies, in which case, a multitude of time dependent impedance spectra are generated. This multitude of time dependent impedance spectra recorded over a period of time wherein each spectrum corresponds to time dependent data at a single characteristic frequency of determination we call a series of time dependent impedance spectra. Typically, a time dependent impedance spectrum will exhibit at least one peak. The peak can be a positive peak or a negative peak. A time dependent impedence spectrum can exhibit a plurality of peaks. The method of deconvoluting a time dependent impedance spectrum involves the assigning to at least one peak of the time dependent impedance spectrum a character corresponding to the measured lubricant property that has peaks in the spectrum that coincide in time.

For the preferred on-line determination of a series of time dependent lubricant properties including but not limited to properties such as additive degradation, base oil oxidation, temperature change, water and other polar species contamination, and viscosity changes of the lubricant oil a series of corresponding lubricant property sensors can be placed into the lubricating oil. Each on-line sensor can measure its characteristic lubricant property over a period of time corresponding to the time the impedance measurements are made. It is preferred to measure the time dependent lubricant properties over the same time range and at the same time interval the time dependent impedence spectra are measured. It is preferred to measure the impedance spectrum and lubricant properties for the period of operation and lifetime of the machinery or system comprising the working fluid. Typically this can range from about 1 day to about 10 years. It is preferred to measure the impedance spectrum and lubricant properties at a time interval in the range of about 12 hours to about 1 year. The preferred time period of measurement is dependent on the time range of measurement. One of ordinary skill in the art can determine the desired time period of measurement.

Using Tables-1 and 2 the invention is further illustrated. Measurement of one lubricant property (for example, P1) as a function of time generates a corresponding lubricant property time dependent spectrum (for example TDSP1). This spectrum will exhibit a positive or negative peak at a specific time (for example, at t1) when the property, P1 undergoes a change. Similarly, measurement of another lubricant property P2 as a function of time in the same time period of measurement will produce a P2 time dependent spectrum TDSP2 exhibiting a peak at t2. Thus for each of lubricant properties P1 to Pn, n number of corresponding time dependent spectra TDSP1 to TDSPn are generated. Each TDSPn can exhibit a characteristic peak at tn. A property-time table (Table-1) can be generated as shown below:

TABLE 1

| Property | Spectra | Time at which peak is observed |
|----------|---------|-------------------------------|
| P1 | TDSP1 | t1 |
| P2 | TDSP2 | t2 |
| Pn | TDSPn | tn |

A time dependent impedance spectrum is generated for same time range and at the same time interval the lubricant properties are measured. This time dependent impedance spectrum can have a number of peaks I1 to In at times t1 to tn. A time dependent impedance spectrum can also be represented in tabular from (Table-2) shown below.

TABLE 2

| Time at which impedance peak is observed | Peak number |
|---|---|
| t1 | I1 |
| t2 | I2 |
| t3 | I3 |
| tn | In |

Figure 3:
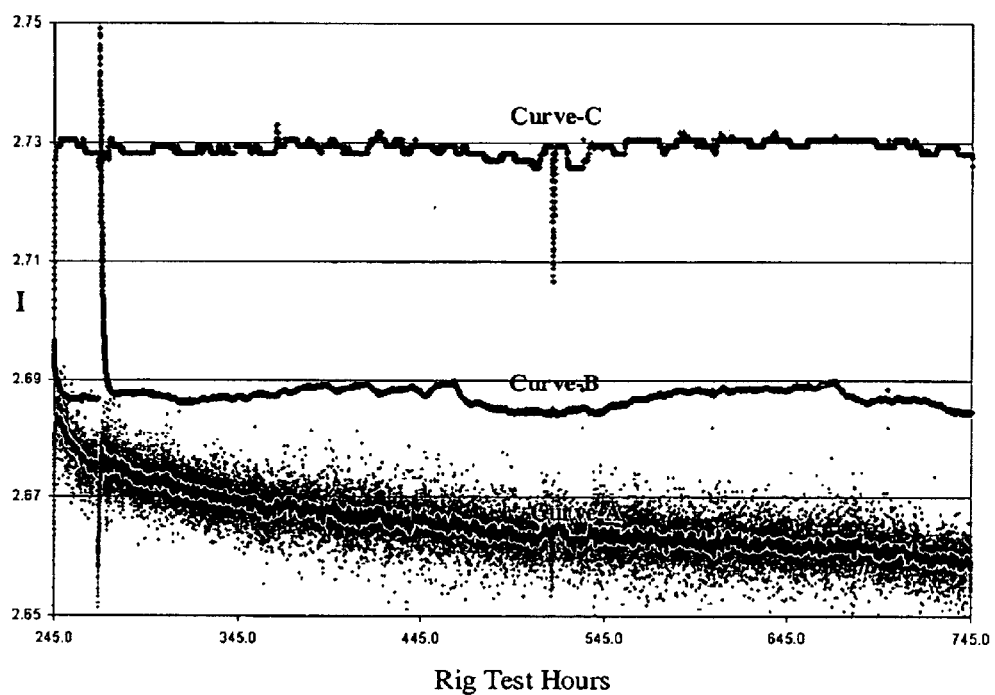
FIG. 3 is a set of experimental data on a machine oil. Curve A is a time dependent dielectric spectrum. Time (in hours) is plotted on the x-axis and the dielectric constant is plotted on the y-axis. Also included in FIG. 3 are water (curve B) and temperature (curve C) time dependent spectra. Relative humidity (water) and temperature are plotted as a function of time on the same x-axis (time in hours).

The property-time table (Table-1) is compared to the time dependent impedance spectrum table (Table-2) and to each impedance peak I1 to In is assigned lubricant property P1 to Pn. It is not essential to assign each and every peak on the impedance spectrum to a lubricant property. Preferably, at least one peak on the impedance spectrum is assigned a lubricant property. More preferably at least two peaks on the impedance spectrum are assigned to lubricant properties. The assignment is made based on the time t1 to tn of occurrence of the peaks by a one—one correspondence method. A non-limiting example of a time dependent dielectric constant spectrum is shown in FIG. 3, curve-A. In this example, peak I1 occurring at time t1 will be assigned property P1, that is, the first peak occurring at about 270 hours is assigned to water in the lube oil.

The time dependent impedance spectrum with at least one peak (I) assigned to a particular lubricant property (P) is the deconvoluted time dependent impedance spectrum. The deconvolution method described above for a single frequency can be applied to each time dependent spectrum of a series of time dependent impedance spectra determined at a multiplicity of frequencies to obtain a series of deconvoluted time dependent impedance spectra.

As described earlier, frequency dependent impedance can be used to determine one or more of the resistance (R), the capacitance (C), the dielectric constant, the frequency at which the phase angle between the voltage and current is 45°, the time constant (or Omega max) of the working fluid. The disclosed method of deconvolution of time dependent impedance spectrum can be applied for the deconvolution of time dependent resistance (R), capacitance (C), dielectric constant and the time constant (or Omega max) spectra as derived from a frequency dependent impedance spectrum. It is preferred to obtain the impedance and lubricant property time dependent spectra on-line and in real time of operation of the machinery under examination. Preferably, the AC elecro-impedance and lubricant property measurements made on low conductivity industrial oils are made at a temperature above about 50° C. and more preferably above about 65° C. and up to about 150° C. It is preferred to determine impedance spectrum in the frequencies range between 1 and 30,000 Hz. More preferably 1 to 10,000 Hz.

In another embodiment of the invention is a method to use a time dependent spectrum as an indicator of the performance condition of a lubricant oil. A time dependent spectrum of the lubricant oil is obtained over a time range and at a plurality of time intervals, wherein said spectrum comprises at least one peak and said spectrum is selected from the group consisting of impedance spectrum, admittance spectrum, resistance spectrum, capacitance spectrum, phase angle spectrum and dielectric spectrum. At least one lubricant property is measured over said time range and at said plurality of time intervals to provide at least one time dependent lubricant property spectrum. Preferably, the measurement of lubricant property is conducted simultaneously with the measurement of the time dependent spectrum of the lubricant oil. The next step involves comparing the obtained time dependent spectrum with the measured time dependent lubricant property spectra. In the case where the peaks of each coincide in time, the comparison includes assigning to the peaks on the time dependent spectrum the lubricant property of the measured coinciding time dependent lubricant properties whereby the time dependent spectrum is used as an indicator of the measured lubricant property. In the case where the peaks of each do not coincide in time, the time dependent spectrum is used as an indicator of reduced performance condition of the lubricant oil.

The lubricant oil can be analyzed using a single deconvoluted time dependent impedance spectrum determined at one frequency. Preferably, the lubricant fluid is analyzed using a series of deconvoluted time dependent impedance spectra determined at a multitude of frequencies.

One reason for the complicated or convoluted nature of impedance spectra is that impedance is a very sensitive measurement and responds to many factors resulting in a time dependent spectra with a multitude of peaks. Factors such as water contamination, temperature change, oil oxidation, and viscosity reduction can be determined simultaneously with the impedence measurements and the peaks corresponding to these can be assigned as disclosed earlier. For example, a reduction in viscosity by a certain factor or ingress of water beyond a threshold amount as indicated from the deconvoluted time dependent impedance, resistance, capacitance, dielectric constant or phase angle spectrum is an indicator of reduced lubricant performance. Occurrence of peaks other than those assigned is an indicator that the performance condition of the lubricant oil is altered.

The method of the instant invention allows the operator of a machinery comprising a working fluid such as a lubricant oil to determine the performance condition of the working fluid. When the performance condition of the working fluid is reduced the operator is signaled or alerted to such change. A long-standing need for such an alert is fulfilled by the method of the instant invention.

In another embodiment of the invention is a method to determine viscosity ratio of a lubricating oil from frequency dependent impedance data. Viscosity ratio (VR) of a lubricating fluid can be expressed as $VR=V_t/V_0$ where $V_t$ is the viscosity of said fluid at any time t after which it is subject to lubrication function and $V_0$ is the initial viscosity at time, t=0.

A method to determine viscosity ratio of a lubricating oil from frequency dependent impedance spectra comprises first measuring frequency dependent impedance data for the lubricating oil and then using the said data to determine one or more of the resistance, the capacitance, the frequency at which the phase angle between the voltage and current is 45° (Omega max), the time constant of the lubricating fluid and dielectric constant using the Nyquist plot. It is preferred to determine the resistance (R) of the lubricating fluid. It is preferred to determine the resistance (R) of the lubricating fluid at time t=0 and any time, t during operation of the machinery comprising the lubricating fluid. The resistance ($R_o$) at time t=0 is the initial resistance of the lubricating fluid. The resistance at any time t is denoted $R_t$. The resistance ratio is calculated and is equal to $R_t/R_o$.

In the second step, the optical density or absorbance (A) of the lubricating oil at time, t is determined at a wavelength in the range of 500 to 1050 nm, preferably in the range of 750 to 975 nm, and more preferable at about 800 nm. The absorbance and resistance measurements are made at the same temperature.

Figure 4:
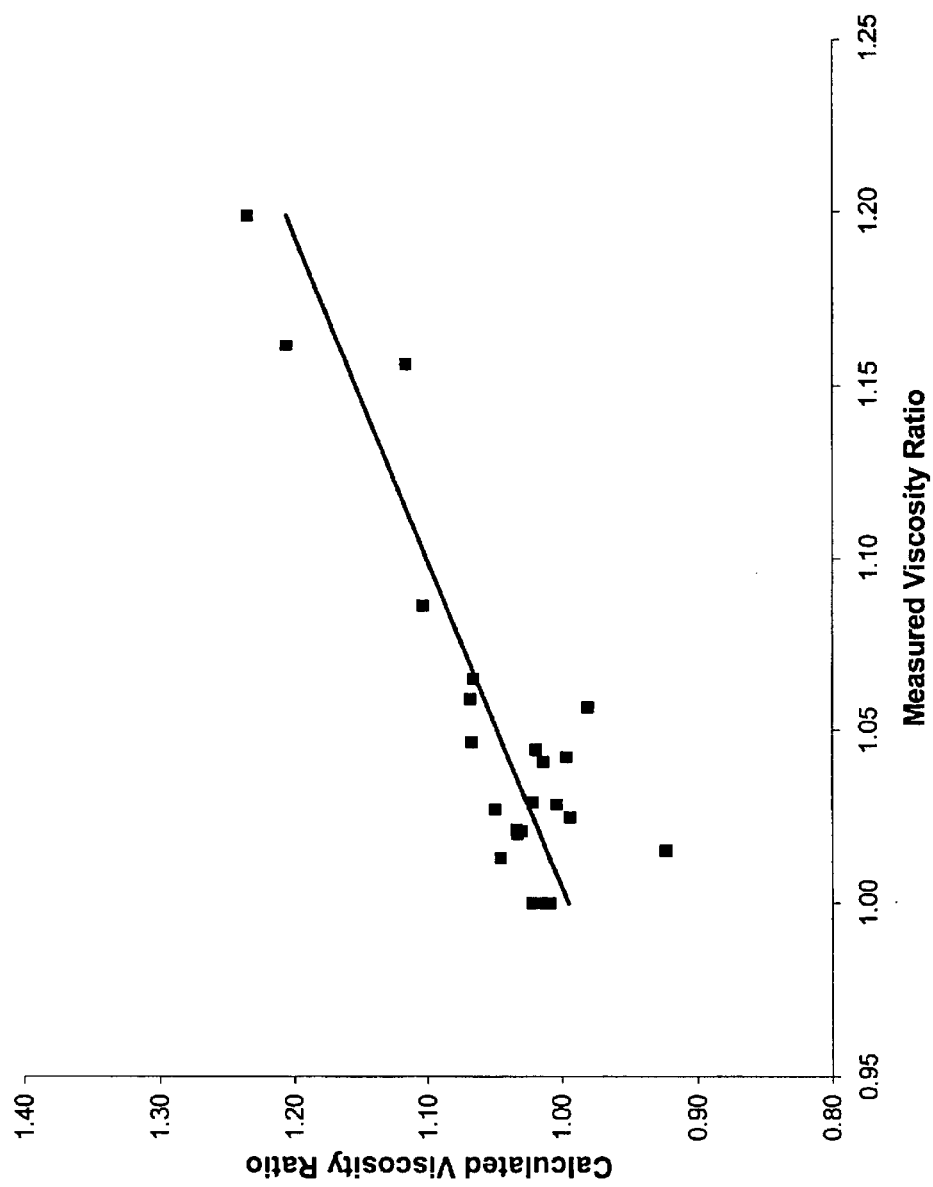
FIG. 4 is a regression plot of calculated viscosity ratio versus measured viscosity ratio for a lubricant oil.

From the measured absorbance (A) at time, t and the resistance ratio (RR) $R_t/R_o$ the viscosity ratio (VR) is determined using the expression:

$VR=\{RR+C1+C2(A-C3)\}/C4$ where C1 C2 and C3 are numbers whose absolute values range from 0 to 10,000. C4 is a number whose absolute value ranges from 0.005 to 10,000. The absolute values of C1, C2, C3 and C4 will depend on the composition of the working fluid. For example, the values of C1, C2, C3 and C4 are 5.481, 0.559, 0.221 and 6.439 respectively for the paper machine oil of Example-2 used to illustrate the instant invention. The values of C1, C2, C3 and C4 can be determined from a regression plot of calculated viscosity ratio versus measured viscosity ratio as illustrated in FIG. 4 and Example-2.

The viscosity ratio (VR) determined using the frequency dependent impedance and absorbance measurements can be used to determine the quality of the lubricant oil. The greater the deviation from unity the poorer the quality of the oil. It is preferred to measure the impedance and absorbance data for the lubricating oil on-line and in real time. It is also preferred to make the impedance and absorbance measurements at the same temperature. The calculated VR is then an on-line viscosity ratio of the lubricant oil. Thus, the lubricant quality can be monitored continuously over the period of working of the machinery comprising the lubricant oil.

The method to determine viscosity ratio of a lubricating oil from frequency dependent impedance data can also be used to determine other properties of the lubricating oil such as and not limited to additive concentration, ingress of foreign particulate concentration and water concentration.

The invention as disclosed in the instant application is applicable to any working fluid that can be subject to impedance measurements and not limited to a lubricant oil. A lubricant oil is one illustrative example of such a working fluid.

EXAMPLES

Example 1

Dielectric constant, relative humidity, and temperature measurements were made for an industrial oil X over a 500 hour time period in a lubricant rig test. Results of this test are shown in FIG. 3 and are represented as curves A, B and C corresponding to dielectric constant, water and temperature respectively. Curve-A shows two distinct changes or peaks. It is to be noted the peaks are negative peaks on the dielectric spectrum (Curve-A). The first change in the dielectric signal corresponding to the first peak is contamination, in this case water. The next observable change is the second peak. This peak can be assigned to a temperature decrease. By combining the two lubricant property sensors in this experimental set these distinctions are made and result in deconvolution of the impedance spectrum. Further, interpretation of the deconvoluted impedance spectrum provides information that the lubricant oil has gradually reduced performance over the course of 500 hour time period.

Example 2

Six different paper machine oils were oxidized by heating them in an oven at 140 C for 12 days with copper and steel rods, which served as catalysts to increase oxidation rate. Periodically samples were withdrawn from the containers and analyzed by measuring their optical absorbance (A) at 800 nm through a 1 cm thick liquid sample. Samples were also analyzed using AC impedance spectroscopy at multiple frequencies and resistance, R, was calculated. Kinematic viscosity was measured for each sample by the ASTM D 455 method. FIG. 4 shows a plot of measured viscosity ratio (viscosity of sample/viscosity of fresh oil ie., oil before commencement of oxidation) determined by the ASTM D 455 method versus the viscosity ratio calculated using the expression: $VR=\{RR+C1+C2(A-C3)\}/C4$ where C1, C2, C3 and C4 are 5.481, 0.559, 0.221 and 6.439 respectively. The observed linearity of the plot is an illustration of one embodiment of the instant invention ie., method to determine viscosity ratio of a lubricating oil from frequency dependent impedance data.

What is claimed is:

1. A method to determine the viscosity ratio of a lubricating oil in a machinery comprising:
    measuring frequency dependent impedance data for the lubricating oil over a range of frequencies and over a time range,
    determining the resistance (R) of the lubricating fluid using a Nyquist plot, at starting time t=0 and a particular time, t within said time range, and denoting the resistance at time t=0 as $R_o$ and the resistance at time t as $R_t$,
    calculating a resistance ratio $RR=R_t/R_o$,
    measuring the absorbance (A) of the lubricating oil at said time, t at a wavelength in the range of 500 to 1050 nm,
    calculating the value of $\{RR+C1+C2(A-C3)\}/C4$ where C1, C2 and C3 are numbers whose absolute values range from 0 to 10,000, and C4 is a number whose absolute value ranges from 0.005 to 10,000,
    said determined value being the viscosity ratio of the lubricating oil.

2. The method of claim 1 wherein said frequency dependent impedance data is measured in the frequency range between 1 and 10,000 Hz.

3. The method of claim 1 wherein said frequency dependent impedance data is measured at more than 2 frequencies to provide a series of frequency dependent spectra.

4. The method of claim 1 wherein said frequency dependent impedance data and absorbance are measured at temperatures in the range of 50° C. to 150° C.

5. The method of claim 1 wherein said frequency dependent impedance data and absorbance are measured on-line the machinery containing the lubricant oil.

6. The method of claim 1 wherein said frequency dependent impedance data and absorbance are measured over a time range of 1 day to 10 years.

7. The method of claim 1 wherein said frequency dependent impedance data and absorbance are measured at a time interval in the range of about 12 hours to about 1 year.

8. The method of claim 1 wherein said absorbance is measured at a wavelength in the range of 750 nm to 975 nm.

* * * * *